US009259312B2

(12) United States Patent
Mensah et al.

(10) Patent No.: US 9,259,312 B2
(45) Date of Patent: Feb. 16, 2016

(54) PHARMACOLOGICAL DELIVERY IMPLEMENT FOR USE WITH CARDIAC REPAIR DEVICES

(71) Applicant: Medtronic, Inc., Minneapolis, MN (US)

(72) Inventors: Eugene A. Mensah, Irvine, CA (US); Mark C. S. Shu, Rancho Santa Margarita, CA (US); Chris M. Coppin, Carlsbad, CA (US)

(73) Assignee: Medtronic, Inc., Minneapolis, MN (US)

( * ) Notice: Subject to any disclaimer, the term of this patent is extended or adjusted under 35 U.S.C. 154(b) by 500 days.

(21) Appl. No.: 13/712,866

(22) Filed: Dec. 12, 2012

(65) Prior Publication Data

US 2013/0103141 A1    Apr. 25, 2013

Related U.S. Application Data

(63) Continuation of application No. 10/819,470, filed on Apr. 7, 2004, now Pat. No. 8,349,001.

(51) Int. Cl.
*A61F 2/24* (2006.01)

(52) U.S. Cl.
CPC .............. *A61F 2/24* (2013.01); *A61F 2/2409* (2013.01); *A61F 2/2412* (2013.01); *A61F 2/2448* (2013.01); *A61F 2/2403* (2013.01); *A61F 2/2445* (2013.01); *A61F 2250/0023* (2013.01); *A61F 2250/0024* (2013.01); *A61F 2250/0068* (2013.01); *A61F 2250/0069* (2013.01)

(58) Field of Classification Search
CPC .............................................. A61F 2250/0068
See application file for complete search history.

(56) References Cited

U.S. PATENT DOCUMENTS

| | | | |
|---|---|---|---|
| 3,571,815 A * | 3/1971 | Somyk | 623/2.4 |
| 3,997,923 A | 12/1976 | Possis | |
| 4,011,947 A * | 3/1977 | Sawyer | 206/363 |
| 4,705,516 A | 11/1987 | Barone et al. | |
| 5,728,152 A | 3/1998 | Mirsch, II et al. | |
| 5,891,108 A | 4/1999 | Leone et al. | |
| 5,895,420 A | 4/1999 | Mirsch, II et al. | |
| 5,910,170 A | 6/1999 | Reimink et al. | |
| 5,948,019 A | 9/1999 | Shu et al. | |
| 5,951,600 A * | 9/1999 | Lemelson | 623/2.11 |
| 6,071,305 A | 6/2000 | Brown et al. | |
| 6,159,240 A | 12/2000 | Sparer et al. | |
| 6,174,332 B1 | 1/2001 | Loch et al. | |
| 6,224,566 B1 | 5/2001 | Loeb | |
| 6,250,308 B1 | 6/2001 | Cox | |

(Continued)

OTHER PUBLICATIONS

Walline et al. "Synthesis of a Thrombin Responsive Drug Delivery Coating for Cardiovascular Stents," Polymer Preprints 2003, 44(1), 193-94.

(Continued)

*Primary Examiner* — Thomas J Sweet
*Assistant Examiner* — Cheryl Miller (57) ABSTRACT

A pharmacological delivery implement for use with cardiac repair devices. The pharmacological delivery implement comprises a porous member defining an outer surface, an internal channel configured to selectively house a pharmacological agent, and a plurality of release holes each extending from the outer surface to the internal channel. Following implantation of the pharmacological delivery implement, at least a portion of the pharmacological agent exits the internal channel through the plurality of release holes.

14 Claims, 8 Drawing Sheets

(56) References Cited

U.S. PATENT DOCUMENTS

| | | | |
|---|---|---|---|
| 6,258,122 B1 | 7/2001 | Tweden et al. | |
| 6,358,247 B1 | 3/2002 | Altman et al. | |
| 6,406,493 B1 | 6/2002 | Tu et al. | |
| 6,425,916 B1 | 7/2002 | Garrison et al. | |
| 6,572,642 B2* | 6/2003 | Rinaldi et al. | 623/1.1 |
| 6,585,767 B1 | 7/2003 | Holley et al. | |
| 6,641,553 B1 | 11/2003 | Chee et al. | |
| 6,752,829 B2 | 6/2004 | Kocur et al. | |
| 7,011,682 B2 | 3/2006 | Lashinski et al. | |
| 7,044,966 B2 | 5/2006 | Svanidze et al. | |
| 7,081,133 B2* | 7/2006 | Chinn et al. | 623/2.41 |
| 7,220,277 B2 | 5/2007 | Arru et al. | |
| 8,021,421 B2* | 9/2011 | Fogarty et al. | 623/2.38 |
| 2001/0049557 A1* | 12/2001 | Chinn et al. | 623/2.36 |
| 2002/0002349 A1* | 1/2002 | Flaherty et al. | 604/164.11 |
| 2003/0065386 A1* | 4/2003 | Weadock | 623/2.38 |
| 2003/0074048 A1* | 4/2003 | Sherry | 623/1.13 |
| 2003/0074058 A1 | 4/2003 | Sherry | |
| 2003/0083646 A1* | 5/2003 | Sirhan et al. | 604/891.1 |
| 2003/0083741 A1* | 5/2003 | Woo et al. | 623/2.2 |
| 2004/0093080 A1 | 5/2004 | Helmus et al. | |
| 2004/0133270 A1 | 7/2004 | Grandt | |
| 2004/0267357 A1* | 12/2004 | Allen et al. | 623/2.11 |
| 2005/0075584 A1* | 4/2005 | Cali | 600/587 |
| 2005/0171593 A1* | 8/2005 | Whirley et al. | 623/1.13 |
| 2005/0187614 A1 | 8/2005 | Agnew | |
| 2005/0203614 A1* | 9/2005 | Forster et al. | 623/2.11 |
| 2005/0246012 A1 | 11/2005 | Henderson | |
| 2006/0184240 A1 | 8/2006 | Jimenez et al. | |

OTHER PUBLICATIONS

Haas et al., "Synthesis of Low Thrombogenic Coating with Horseradish Peroxidase," Polymer Preprints 2003, 44 (1), 195.

Macdonald et al., "Diffusion in Transient Polymer Networks: Solvent, Solute and Polymer," Polymer Preprints 2003, 44(1), 289-90.

Von Meerwall et al. "Understanding Diffusion in Entangled Polymer Blends," Polymer Preprints 2003, 44(1), 287-88.

Olanoff et al., "Controlled Release of Tetracycline I: In Vitro Studies with a Trilaminate 2-Hydroxyethyl Methacrylate-Methyl Methacrylate System" J. Pharm. Sci., 1979, 68(9):1147-50.

Olanoff et al, "Controlled Release of Tetracycline II: Development of an In Vivo Flow-Limited Pharmacokinetic Model," J. Pharm. Sci 1979 68(9): 1151-5.

Olanoff et al., "Sustained Release of Nitidazole from Silicone Rubber Implants for the Treatment of Schistosoma Mansoni Infections," Am. J. Trop Med. Hyg. 29(1), 1980, pp. 71-73.

* cited by examiner

PHARMACOLOGICAL DELIVERY IMPLEMENT FOR USE WITH CARDIAC REPAIR DEVICES

CROSS REFERENCE TO RELATED APPLICATIONS

This application is a continuation of U.S. patent application Ser. No. 10/819,470 filed Apr. 7, 2004, now U.S. Pat. No. 8,349,001, the disclosure of which is herein incorporated by reference in its entirety.

The present invention relates to a pharmacological delivery implement. More particularly, the present invention relates to a pharmacological delivery implement for use with repair devices implantable within the cardiac system.

Cardiac repair devices, such as prosthetic valves, annuloplasty prosthesis, vascular grafts, etc., have conventionally been implanted into the heart or surrounding vessels to repair or strengthen diseased or ailing members of the cardiac system. However, many of the cardiac repair devices include prosthetic materials that are not native to the internal system of patients. As such, a patient often has an adverse reaction to the implantation of non-native materials causing chronic inflammation and excessive scar tissue, i.e. pannus.

Various types of prosthetic heart valves, used to replace diseased natural human heart valves, are known in the art. The actual shape and configuration of any particular prosthetic heart valve is, of coarse, dependent to some extent upon the valve being replaced (i.e. mitral valve, tricuspid valve, aortic valve, and pulmonary valve). In general terms, however, the prosthetic heart valve design attempts to replicate the function of the heart valve being replaced and thus will include valve leaflet-like structures. With this in mind, prosthetic heart valves including valve leaflets are generally categorized as either forming relatively flexible leaflets or relatively rigid leaflets.

The category including prosthetic heart valves formed with relatively flexible leaflets includes bioprosthetic heart valves having a substantially annular, fabric-covered stent supporting a number of leaflets made of a biological (e.g. porcine, pericardial tissue, etc.) or synthetic (e.g. polymeric) material. Prosthetic heart valves categorized as forming relatively rigid leaflets include mechanical prosthetic heart valves. A typical mechanical heart valve includes an annular valve housing or body to provide a passageway for blood flow. Relatively rigid leaflets are rotatably mounted to the annular housing and rotate to open or close the blood flow passageway.

Both flexible and rigid leaflet prosthetic heart valves typically include an annularly-extending, flexible sewing ring attached to the fabric-covered stent or valve housing, respectively. Upon implantation of the prosthetic heart valve, the sewing ring is attached to the heart valve annulus surrounding the heart valve to be repaired, thereby, attaching the entirety of the prosthetic heart valve to the heart valve annulus.

During use of a prosthetic heart valve, inflammation can occur and fibrotic scar tissue may form. The fibrotic scar tissue can extend from the sewing ring to the valve leaflets, thereby, causing stenosis and/or regurgitation. Upon occurrence of any such problems, a prosthetic heart valve is typically removed and replaced with a new prosthetic heart valve. In particular, flexible leaflet prosthetic heart valves experiencing inflammation, stenosis, and/or regurgitation must be removed in the relatively near future to prevent further harm to the heart valve and surrounding material.

Due to the mechanical attributes of the mechanical valve, a mechanical valve causing inflammation, stenosis, and/or regurgitation must be removed almost immediately following detection of a problem in order to prevent dire consequences to the patient. Even if prosthetic valve removal can be performed before such dire consequences occur, the removal and replacement procedure once again exposes the patient to the general dangers of surgery along with additional periods of heart stoppage. Due to the complicated nature of the heart vessel, it is difficult to deliver pharmacological agents targeted to the heart valve annuls tissue to decrease inflammation, stenosis, regurgitation, etc.

Annuloplasty prosthesis, generally categorized as either annuloplasty rings or annuloplasty bands, are employed in conjunction with valvular reconstructive surgery to assist in the correction of heart valve defects such as stenosis and valvular insufficiency. The purpose of the annuloplasty prosthesis is to restrict and/or support the heart valve annulus to correct and/or decrease valvular insufficiency. A posterior portion of the annulus is often diseased or dilated and not well supported by heart tissue. An anterior portion of the annulus, in contrast, is well supported by surrounding heart tissue.

In general terms, annuloplasty rings completely encompass both the anterior and posterior portions of the valve annulus. Annuloplasty bands, on the other hand, are specifically designed to primarily encompass only a portion of the valve annulus. For example, an annuloplasty band may be configured to encompass only the posterior portion of the valve annulus, thus promoting natural movement of the anterior portion of the heart valve annulus.

Inflammation and excessive scar tissue also typically form on annuloplasty prostheses causing similar problems as described above with respect to prosthetic heart valves. Also similar as described above, angioplasty prosthesis causing excessive inflammation or scar tissue typically most be explanted and replaced, thereby, introducing the patient to the dangers presented by additional surgeries including anesthesia, infection, extended periods of heart stoppage, etc. Similar problems, as those discussed above with respect to prosthetic heart valves and annuloplasty prostheses, can be caused with other cardiac repair devices such as vascular grafts, etc.

As described above, implantation of prosthetic heart valves, annuloplasty bands, and other cardiac repair devices may lead to excessive inflammation, scar tissue, stenosis, and/or regurgitation. As such, a need exists for a cardiac repair device that prevents or decreases the occurrence of inflammation, excessive sear tissue, stenosis, and/or regurgitation, thereby, decreasing the need for explanation of the cardiac repair devices that, in turn, decreases the dangers to which a particular patient is exposed.

SUMMARY OF THE INVENTION

One aspect of the present invention relates to a pharmacological delivery implement for use with cardiac repair devices. The pharmacological delivery implement comprises a porous member defining an outer surface, an internal channel configured to selectively house a pharmacological agent, and a plurality of release holes each extending from the outer surface to the internal channel. Following implantation of the pharmacological delivery implement within the cardiac system, at least a portion of the pharmacological agent exits the internal channel through the plurality of release holes.

Another aspect of the present invention relates to a cardiac repair device including a porous member and a fabric sheath. The porous member defines an outer surface, an internal channel, and a plurality of release holes. The internal channel is configured to selectively house a pharmacological agent. The plurality of release holes each extend from the outer surface to the internal channel. The fabric sheath encompasses the porous member. Following implantation of the cardiac repair device, at least a portion of the pharmacological agent exits the internal channel through the plurality of release holes.

Yet another aspect of the present invention relates to a method of delivering a pharmacological agent to cardiac tissue. The method includes providing a porous member defining an internal channel configured to selectively maintain a pharmacological agent, filling the channel with a pharmacological agent, and implanting the porous member filled with the pharmacological agent within a cardiac system. The porous member further defines an outer surface and a plurality of release holes each extending from the outer surface to the internal channel. Upon functioning of the cardiac system, at least a portion of the pharmacological agent exits the internal channel via the plurality of release holes.

DETAILED DESCRIPTION OF THE PREFERRED EMBODIMENTS

Figure 1:
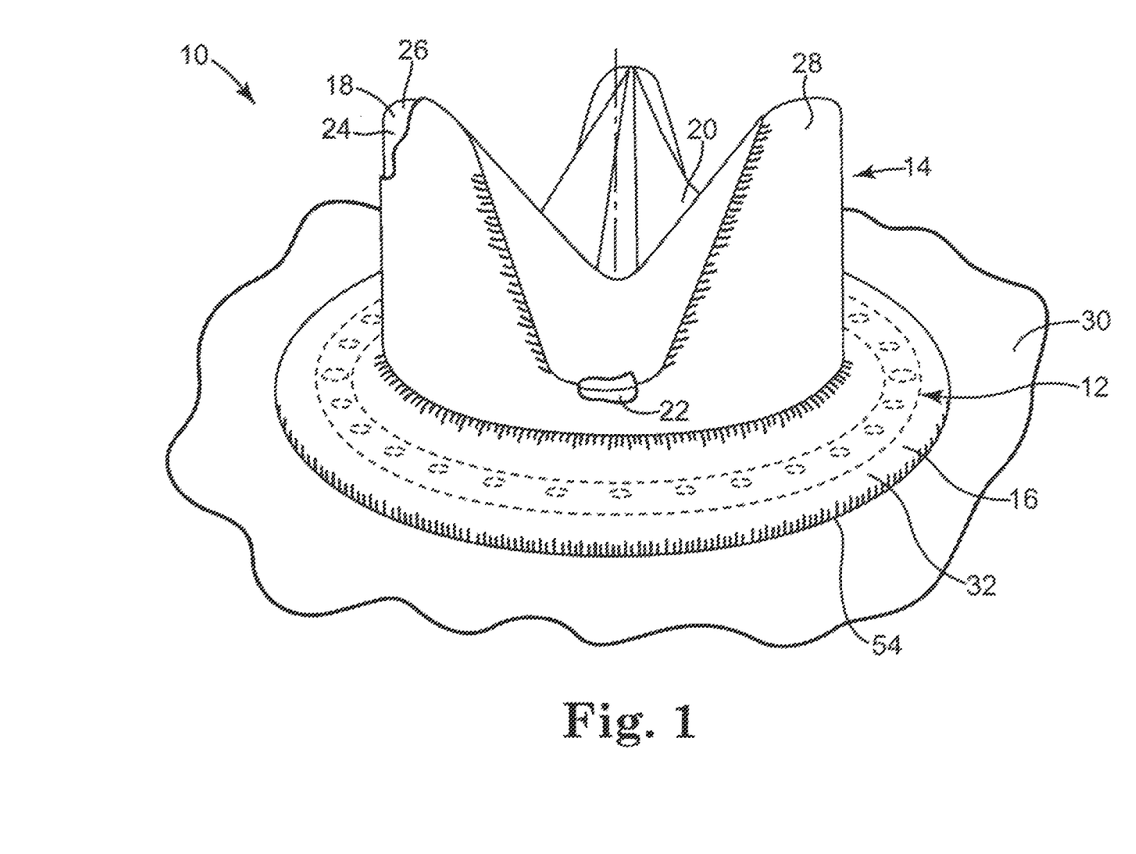
FIG. 1 is a perspective view of one embodiment of a heart valve prosthesis incorporating a pharmacological delivery implement in accordance with the present invention.

One preferred embodiment of a heart valve prosthesis 10 incorporating a pharmacological delivery implement 12 is illustrated in FIG. 1. The heart valve prosthesis 10 generally includes a valve body 14 and a sewing ring 16. In one embodiment, the heart valve prosthesis 10 is a flexible leaflet heart valve prosthesis 10. Valve body 14 includes a stent 18 and leaflets 20. The stent 18 provides the support framework for the heart valve prosthesis 10. The stent 18 includes an inner frame member or stent ring 22, which typically defines a circular or parabolic ring, and stent posts 24. Each of the stent posts 24 extends from the stent ring 22 and terminates in a rounded tip or free end 26 opposite the stent ring 22. The stent posts 24 are formed of a stiff but resiliency bendable material. Valve body 14 further includes a cloth cover 28, which is preferably formed over the stent ring 22 and the stent posts 24. The cloth cover 28 is formed of a biocompatible, fabric material.

Each of the leaflets 20 is sutured to the cloth cover 28. In particular, the leaflets 20 are sutured to the cloth cover 28 that covers the stent posts 24 such that each leaflet 20 extends between two of the stent posts 24. Each of the leaflets 20 is also sutured to the cloth cover 28 covering the stent ring 22 between the two stent posts 24. The leaflets 20 are made of a biological (e.g. porcine, pericardial, etc.) or synthetic (e.g. polymeric) material and are configured to open and close to regulate blood flow through the heart valve prosthesis 10 when implanted.

The sewing ring 16 is coupled to and extends around the stent ring 22 opposite the stent post 24. The sewing ring 16 is formed of a tubular cloth covering 32, which is similar to the cloth covering 28 attached to the stent 18. The cloth covering 32 is sutured to the cloth covering 28 of the stent 18 about the outer perimeter of the stent ring 22 opposite the extension of the stent posts 24.

Figure 2:
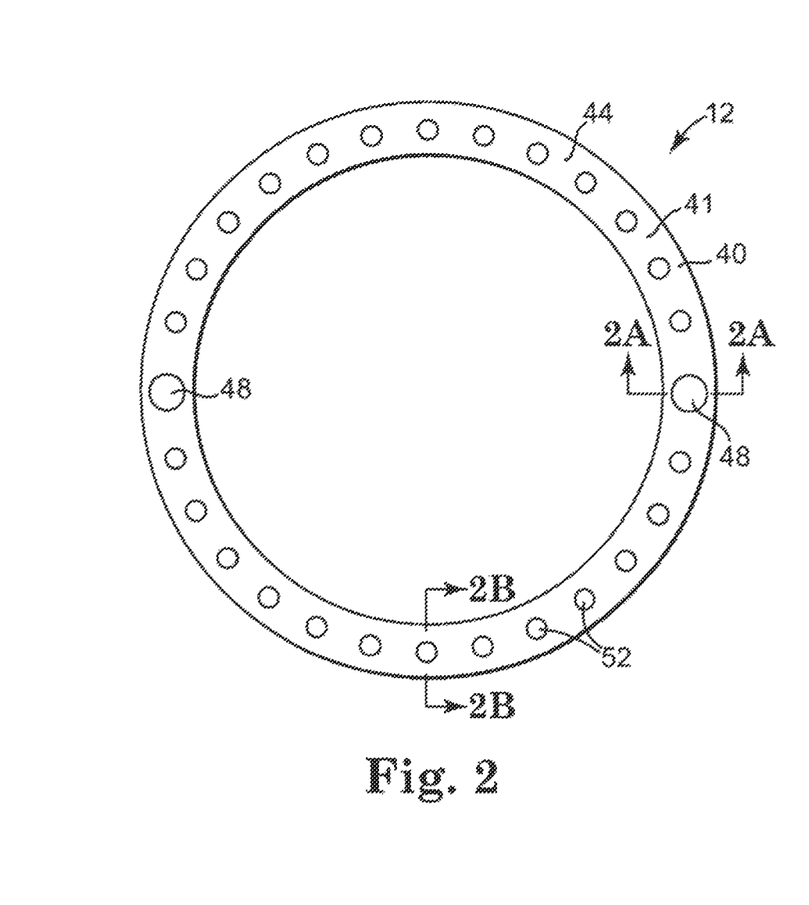
FIG. 2 is a top view of one embodiment of the pharmacological delivery implement of FIG. 1.

In one embodiment, the pharmacological delivery implement 12 is encased within the cloth covering 32 of the sewing ring 16. As best illustrated in FIG. 2 with additional reference to the cross-sectional FIGS. 2A and 2B, the pharmacological delivery implement 12 includes a substantially annular, porous member 40 defining an outer surface 41 having an inflow side 42 and an outflow side 44. The annular porous member 40 defines a porosity and a permeability great enough to allow blood flow through the annular porous member 40 from the inflow side 42 to the outflow side 44.

Figure 2A:
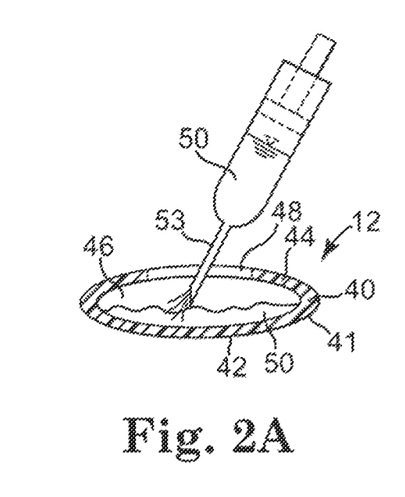
FIG. 2A is a cross-sectional view of the pharmacological delivery implement of FIG. 2 taken along the line 2A-2A.
Figure 2B:
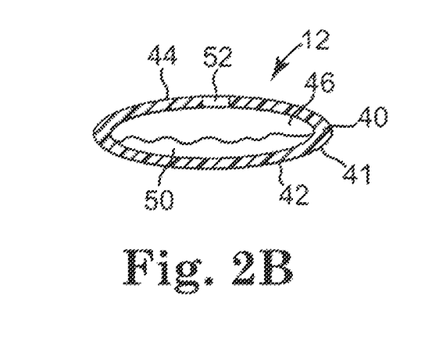
FIG. 2B is a cross-sectional view of the pharmacological delivery implement of FIG. 2 taken along the line 2B-2B.

The annular porous member 40 further defines an internal channel 46 and at least one injection site 48. In one embodiment, the internal channel 46 is formed as an annular lumen within annular porous member 40. The internal channel 46 is sized to receive and selectively maintain a pharmacological agent 50, such as an anti-inflammatory drug, etc. In particular, the at least one injection site 48 is formed on the outer surface 41 of the annular porous member 40. In one embodiment, the at least one injection site 48 is formed on the outflow side 44 of the annular porous member 40. The injection site 48 provides access from the outer surface 41 to the internal channel 46. In one embodiment, the annular porous member 40 defines at least two injection sites 48 to facilitate proper injection of the pharmacological agent 50 within the internal channel 46 without providing for escape of the pharmacological agent 50 from the release holes 52 or other injection sites 48. In one embodiment, the annular porous member 40 includes two injection sites 48 positioned opposite one another on the annular porous member 40.

In one embodiment, the annular porous member 40 defines a porosity and a permeability low enough to maintain the pharmacological agent 50 for a desired length of time (e.g., 2 hours, 2 weeks, or 2 months). In particular, in one embodiment, the annular porous member 40 has a porosity and permeability dependent upon the viscosity of the pharmacological agent 50 in order to selectively maintain the pharmacological agent 50 for a desired length of time. In one embodiment, the annular porous member has a porosity and permeability dependent upon the elution profile of the pharmacological agent 50. In addition, in one embodiment, the porosity and permeability of the annular porous member 40 is determined at least in part by the expected protein growth upon the annular porous member 40 following implantation.

The annular porous member 40 further includes a plurality of release holes 52 extending from the outer surface 41 to the internal channel 46. In one embodiment, at least a portion of the plurality of release holes 52 extend from the outflow side 44 of the outer surface 41 to the internal channel 46. The release holes 52 are sized to allow escape of the pharmacological agent 50 from the internal channel 46 upon mixing with blood, as will further be described below. In one embodiment, at least a portion of the release holes 52 are inherently formed by the porosity of the annular porous member 40. In one embodiment, at least a portion of the release holes 52 are drilled, punched, or otherwise formed and placed on the outer surface 41 in addition to the general porosity of the annular porous member 40. In one embodiment, the annular porous member 40 is formed of an elastomeric polymer. In one embodiment, the annular porous member 40 is formed of silicone.

Figure 3:
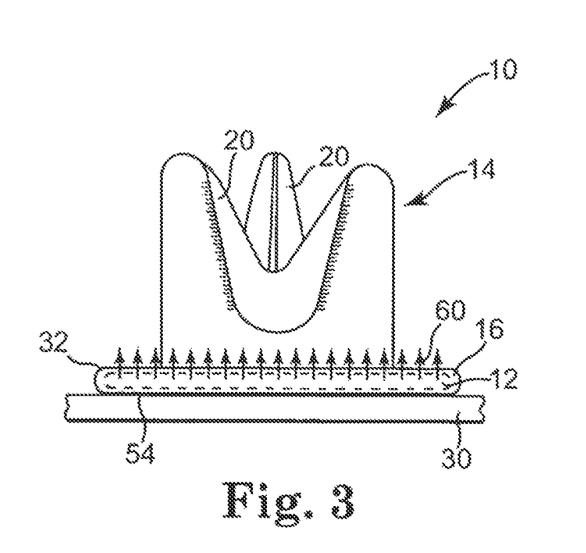
FIG. 3 is a side view of one embodiment of the heart valve prosthesis of FIG. 1.

As shown in FIGS. 1 and 3, annular porous member 40 is embedded within the cloth cover 32 of the sewing ring 16. In one embodiment, the sewing ring 16 further includes biocompatible cushion or stuffing material (not shown) disposed within the tubular cloth covering 32 along side the pharmacological delivery implement 12. In one embodiment, the sewing ring 16 may further include an additional support ring (not shown) disposed within the cloth cover 32 to provide additional support to the heart valve prosthesis 10.

During use, a medical team member (not shown) accesses the heart valve prosthesis 10 including the pharmacological delivery implement 12. In one embodiment, accessing the heart valve prosthesis 10 includes removing the heart valve prosthesis 10 from a glutaraldehyde solution (not shown). Notably, the glutaraldehyde solution complicates storage of the pharmacological agent 50 within the porous member 40. Therefore, following removal of the heart valve prosthesis 10 from the glutaraldehyde solution, the medical team member injects the pharmacological agent 50 into the internal channel 46 via at least one injection site 48. In one embodiment, in which the annular porous member 40 includes two injection sites 48, half of the pharmacological agent 50 is injected into the internal channel 46 via one injection site, and the remaining half of the pharmacological agent 50 is injected into the internal channel 46 via the opposing injection site 48.

Following injection, the pharmacological agent 50 is maintained within the internal channel 46. With this is mind, the viscosity of the pharmacological agent 50 and the porosity and permeability of the annular porous member 40 are such that the pharmacological agent 50 does not escape from the internal channel 46 prior to implantation within a heart valve replacement patient (not shown). In one embodiment, the pharmacological agent 50 has a gel or paste form to further support maintenance of the pharmacological agent 50 within the internal channel 46.

Upon injection of the pharmacological agent 50 into the internal channel 46, the heart valve prosthesis 10 is implanted into a patient's heart (not shown). In particular, the heart valve prosthesis 10 is intra-annularly or supra-annularly implanted and attached to the heart valve annulus 30. In particular, in one embodiment, an inflow side 54 of the sewing ring 16 is placed to abut the heart valve annulus 30. The sewing ring 16 is subsequently sutured to the heart valve annulus 30.

Following suturing of the heart valve prosthesis 10 to the heart valve annulus 30, the heart is reactivated and the patient is closed. During use of the heart including the heart valve prosthesis 10, blood flow, generally indicated in FIG. 3 by arrows 60, flows through the heart valve opening (not shown) and the valve body 14 of the heart valve prosthesis 10.

As blood periodically flows through the valve body 14, pressure surrounding the heart valve eventually causes the sewing ring 16 to be partially penetrated by blood. Blood moving through the sewing ring also penetrates the annular porous member 40 and mixes with the pharmacological agent 50 maintained within the internal channel 46 of the delivery vehicle 12. Blood mixing with the pharmacological agent 50 continues to move through and out the annular porous member 40, in particular, the release holes 52 and through the cloth covering 32. As such, the pharmacological agent 50 is transported out of the internal channel 46, gradually exiting the release holes 52, and contacting the surrounding heart valve annulus tissue 30. Interaction between the pharmacological agent 50 and the annulus tissue 30 permit the pharmacological agent 50 to treat and decrease inflammation of, and/or scar tissue growth on the annulus tissue 30 and other surrounding cardiac tissue.

Alternatively, or in addition to the transportation of the pharmacological agent 50 via blood flow 60, the pharmacological agent 50 is transported out of the internal channel 46 by general diffusion. In particular, general patient movement (whether internal and/or external) gradually causes the pharmacological agent 50 to exit the release holes 52 to interact with the surrounding heart tissue. As described above, interaction between the pharmacological agent 50 and the annulus tissue 30 permit the pharmacological agent 50 to treat and decrease inflammation of, and/or scar tissue growth on the annulus tissue 30 and other surrounding cardiac tissue.

Figure 4:
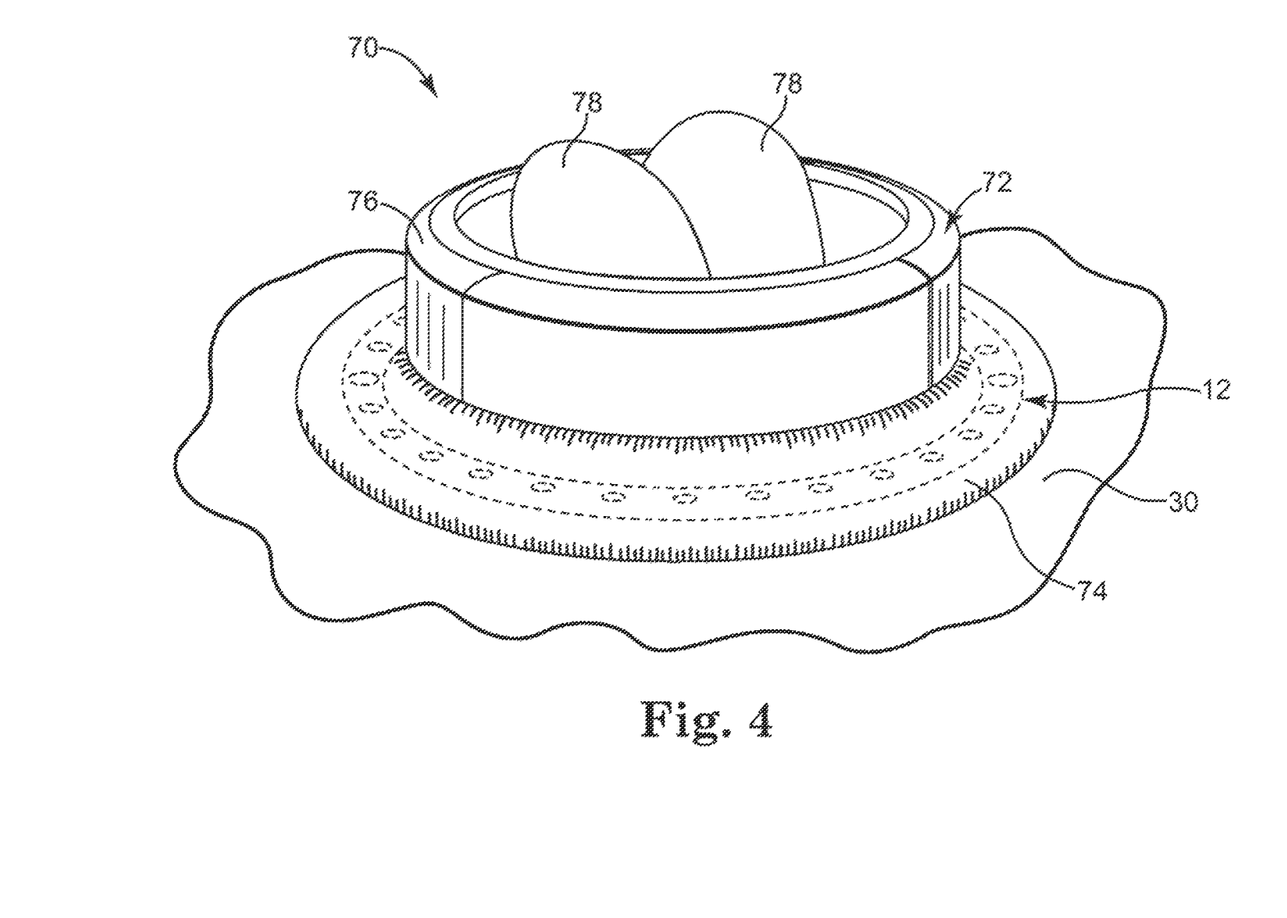
FIG. 4 is a perspective view of one embodiment of a heart valve prosthesis incorporating a pharmacological delivery implement in accordance with the present invention.

FIG. 4 illustrates another embodiment of a heart valve prosthesis 70, in which the heart valve prosthesis 70 is a mechanical heart valve. The heart valve prosthesis 70 includes a valve body 72 and a sewing ring 74. The valve body 72 includes an annular housing 76 and rigid leaflets 78. The annular housing 76 is rigid and substantially hollow. The rigid leaflets 78 are attached within the annular housing 76 in a rotatable or pivotable fashion to open and close the annular housing 76. The sewing ring 74 extends from one edge of the annular housing 76 in a similar manner as described with respect to the stent ring 22 above. The sewing ring 74 is substantially similar to the sewing ring 16, and as such, includes a pharmacological delivery implement 12 also described above.

The heart valve prosthesis 70 is used and functions in a similar manner as described above with respect to the heart valve prosthesis 10. Notably, however, the mechanical heart valve prosthesis 70 is not stored in glutaraldehyde solution. Therefore, in one embodiment, the pharmacological agent 50 is injected into pharmacological delivery implement 12 prior to storing the mechanical heart valve prosthesis for subsequent implantation.

Figure 5:
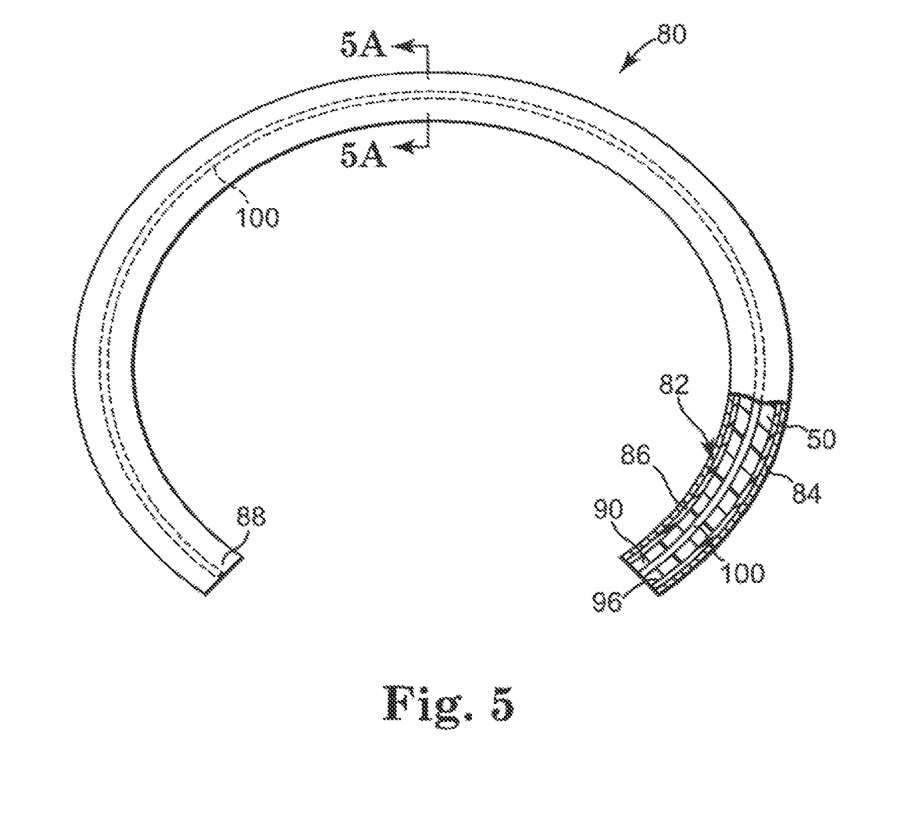
FIG. 5 is a top view of one embodiment of an annuloplasty prosthesis incorporating a pharmacological delivery implement in accordance with the present invention.
Figure 5A:
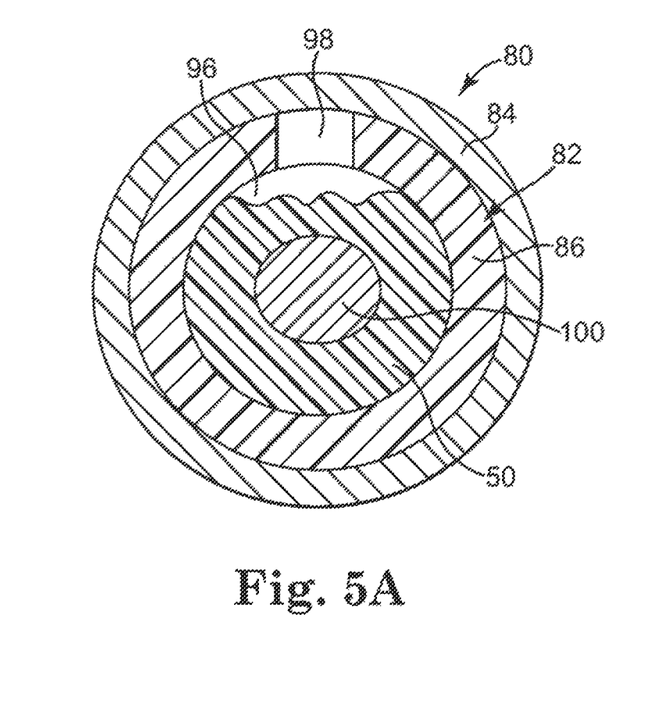
FIG. 5A is a cross-sectional view of one embodiment of the annuloplasty prosthesis of FIG. 5 taken along the line 5A-5A.

FIGS. 5 and 5A illustrate one embodiment of an angioplasty prosthesis 80. In one embodiment, the annuloplasty prosthesis 80 is an annuloplasty band. The annuloplasty prosthesis 80 includes the pharmacological delivery implement 82 extending in an arcuate manner and a cloth cover or sheath 84 enclosing the pharmacological delivery implement 82.

The pharmacological delivery implement 82 includes a porous member 86 which not only forms a portion of pharmacological delivery implement 82 but also provides shape, stiffness, and support to the annuloplasty prosthesis 80. In particular, the porous member 86 is a generally arcuate member encompassed within the cloth sheath 84. The porous member 86 extends from a first end 88 to a second end 90. In one embodiment, each end 88 and 90 defines an eyelet or an opening (not shown) with substantially closed perimeter but does not require a specific shape (e.g. an eyelet can be round, square, rectangular, trapezoidal, hexagonal, tear-drop, oval, elliptical, or any other suitable shape, although shapes with lower stress concentration and rounded features are generally preferred). Each of the eyelets are adapted to receive at least one suture (not shown) to secure the annuloplasty prosthesis 80 to a heart valve annulus 30 (FIG. 6) of a heart valve.

Other features of the pharmacological delivery implement 82 are similar to the features described with respect to the pharmacological delivery implement 12 described above. With this in mind, pharmacological delivery implement 82 similarly defines an internal channel 96, at least one injection site 98 (FIG. 5A), and a plurality of release holes (not shown).

Figure 5B:
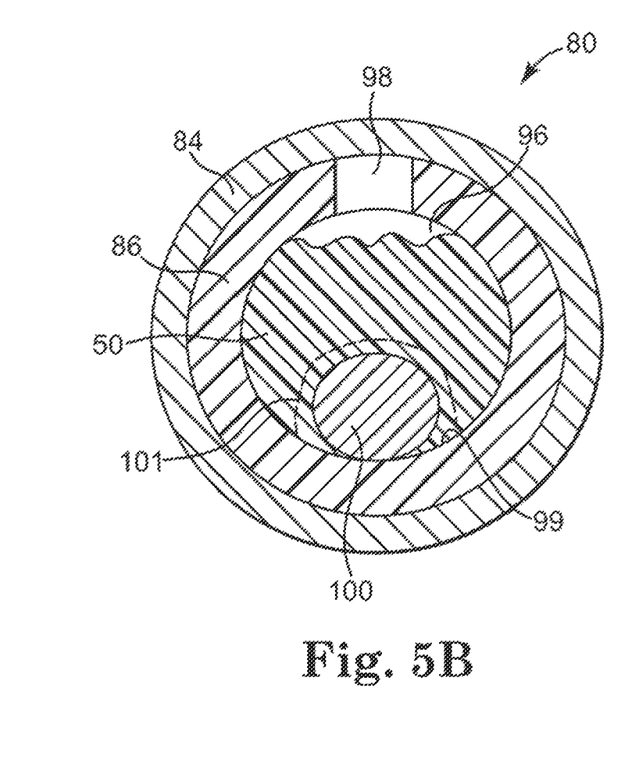
FIG. 5B is an alternate cross-sectional view of one embodiment of the annuloplasty prosthesis of FIG. 5 taken along the line 5A-5A.

In one embodiment, pharmacological delivery implement 82 additionally includes an optional metallic wire 100 extending throughout the internal channel 96. The metallic wire 100 provides additional stiffness and support to the annuloplasty prosthesis 80. In one embodiment, the metallic wire 100 is formed of a biocompatible metal, such as nitinol or a cobalt alloy (e.g., MP35N® made from cobalt-35, nickel-20, chromium-10, and molybdenum and manufactured by SPS Technologies, Inc. of Jenkintown, Pa.). In an alternate embodiment, as illustrated in the cross-sectional view of FIG. 5B, the metallic wire 100 extends through the internal channel 96 and is anchored to an internal surface 99 of the porous member 86. In one embodiment, the porous member 86 optionally forms an extension as generally indicated by the hidden lines 101 encompassing the metallic wire 100 and, thereby, maintaining metallic wire 100 in a static position with respect to the remainder of the porous member 86. Notably, the positioning of the metallic wire 100 does not block the path of the injection hole 98 to the internal channel 96.

The pharmacological agent 50 is injected through the injection site 98 into the internal channel 96. In one embodiment, the pharmacological agent 50 is injected into the internal channel 96 prior to storing the pharmacological delivery implement 82 for subsequent use. In one embodiment, the pharmacological agent 50 is injected into the internal channel 96 just prior to implantation.

Figure 6:
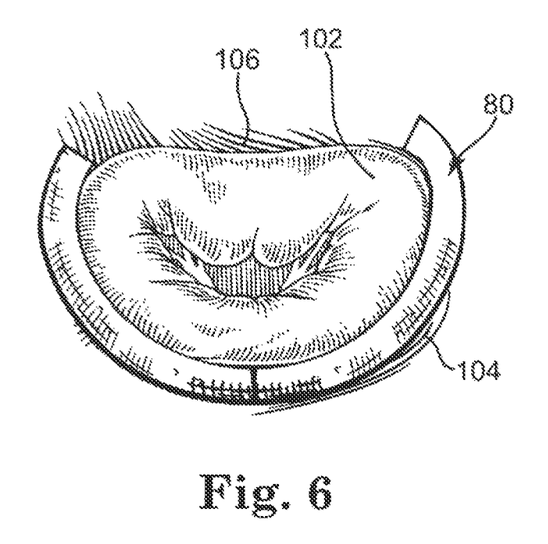
FIG. 6 is a top view of the annuloplasty prosthesis of FIG. 5 mounted on a heart valve annulus.

With additional reference to FIG. 6, the annuloplasty prosthesis 80 filled with the pharmacological agent 50 is subsequently implanted into a heart (not shown), more particularly to a heart valve annulus 30 about a heart valve 102. More specifically, the annuloplasty prosthesis 80 is sutured to and supports a posterior portion 104 of the heart valve annulus 30. With this in mind, the annuloplasty prosthesis 80 does not extend across an anterior portion 106 of the heart valve annulus 30.

Following implantation, during use of the heart, blood flows through the heart valve 102. As the blood surrounds and moves past the annuloplasty prosthesis 80, blood gradually penetrates the cloth sheath 84 and the pharmacological delivery implement 82 to interact with the pharmacological agent 50. As additional blood penetrates the annuloplasty prosthesis 80 and blood escapes the annuloplasty prosthesis 80, the blood moving through the annuloplasty prosthesis 80 mixes with the pharmacological agent 50 and releases the pharmacological agent 50 from the pharmacological delivery implement 82 and from the angioplasty prosthesis 80. In particular, as the blood moves through the annuloplasty prosthesis 80, the blood and the pharmacological agent 50 gradually exits the annuloplasty prosthesis 80, namely through the plurality of release holes (not shown). The blood mixed with pharmacological agent 50 escaping the annuloplasty prosthesis 80 contacts the surrounding heart tissue (not shown), thereby, delivering the pharmacological agent 50 to the surrounding heart tissue to treat and decrease inflammation, scar tissue growth, stenosis, and other undesired conditions.

Alternatively, or in addition to the transportation of the pharmacological agent 50 via blood flow, the pharmacological agent 50 is transported out of the internal channel 96 by general diffusion. In particular, general patient movement (whether internal and/or external) gradually causes the pharmacological agent 50 to exit the release holes (not shown) to interact with the surrounding heart tissue (not shown). As described above, interaction between the pharmacological agent 50 and the annulus tissue 30 permit the pharmacological agent 50 to treat and decrease inflammation of, and/or scar tissue growth on the annulus tissue 30 and other surrounding cardiac tissue.

Figure 7:
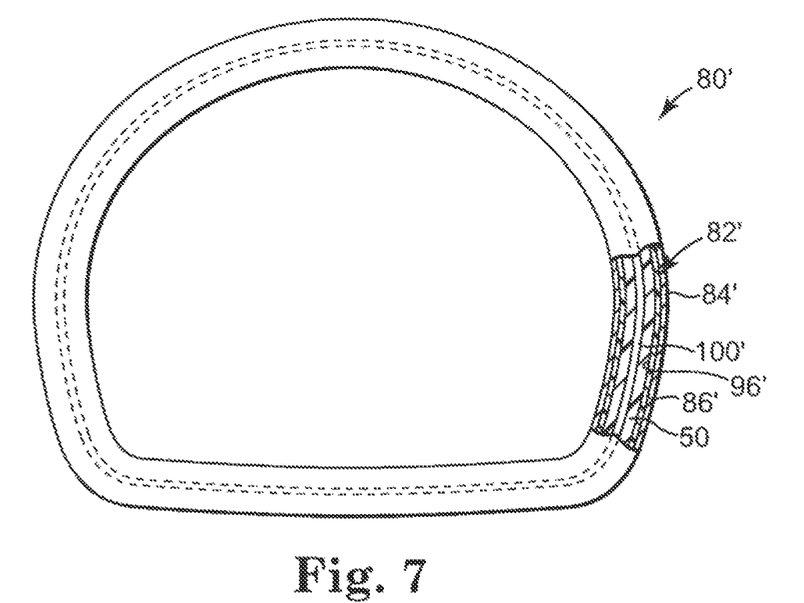
FIG. 7 is a top view of one embodiment of an annuloplasty prosthesis incorporating a pharmacological delivery implement according to the present invention.

FIG. 7 illustrates another embodiment of annuloplasty prosthesis 80' in which the annuloplasty prosthesis 80' is an annuloplasty ring. The annuloplasty ring 80' is formed and includes a pharmacological delivery implement 82' in a similar manner as described above with the annuloplasty prosthesis 80 and pharmacological delivery implement 82. The only difference between the annuloplasty prosthesis 80' and the annuloplasty prosthesis 80 is that the pharmacological delivery implement 82' including a porous member 86' and the cloth sheath 84' each form a closed annular or D-shaped annuloplasty prosthesis 80' rather than a partially annular or merely arcuate annuloplasty prosthesis 80.

An internal channel 96' is formed within and runs throughout the porous member 86'. In one embodiment, the pharmacological delivery implement 82' further includes a metallic wire 100', similar to the metallic wire 100, encompassed by and extending throughout the entire annular or D-shaped porous member 86'. The metallic wire 100' adds rigidity and strength to the annuloplasty prosthesis 80'. With this in mind, the angioplasty prosthesis 80' functions in a similar manner as described above with respect to the annuloplasty prosthesis 80. However, upon implantation, the annuloplasty prosthesis 80' extends along both the posterior portion 106 (FIG. 6) and the anterior portion 108 (FIG. 6) of the heart valve annulus 30 (FIG. 6).

Figure 8:
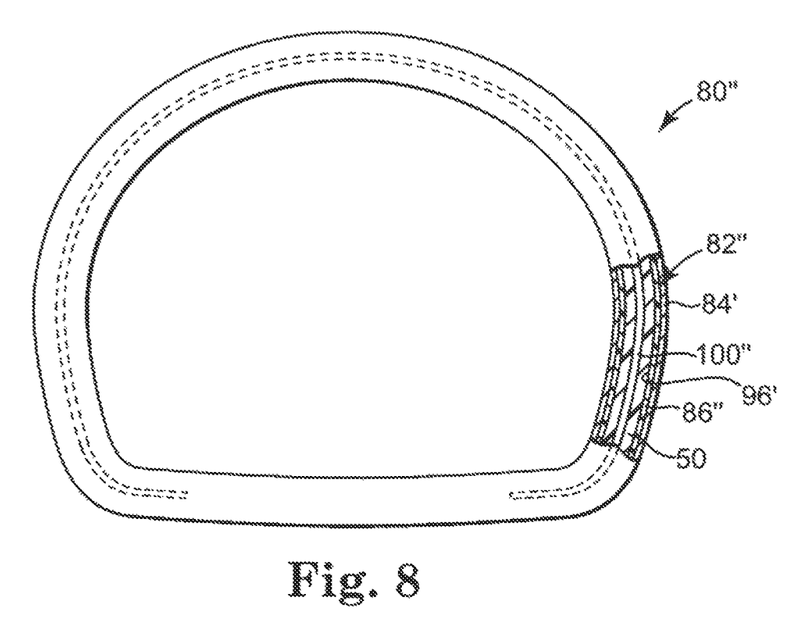
FIG. 8 is a top view of one embodiment of an annuloplasty prosthesis incorporating a pharmacological delivery implement according to the present invention.

FIG. 8 illustrates another embodiment of an annuloplasty prosthesis 80" in which the annuloplasty prosthesis 80" is an annuloplasty ring. The annuloplasty ring 80" is formed and includes a pharmacological delivery implement 82" in a similar manner as described above with respect to the annuloplasty prosthesis 80' including a pharmacological delivery implement 82'. With this is mind, the pharmacological delivery implement 82" is encompassed within a cloth sheath 84'. The pharmacological delivery implement 82" includes a porous member 86" forming an internal channel 96'.

The pharmacological delivery implement 82' further includes a metallic wire 100", similar to the metallic wire 100', encompassed by and extending throughout a portion of the annular or D-shaped porous member 86". In particular, the metallic wire 100" extends throughout the portion of the annuloplasty prosthesis 80" corresponding with the posterior portion 106 (FIG. 6) of the heart valve annulus 30 (FIG. 6) but does not extend through the portion of the annuloplasty prosthesis 80" corresponding with the anterior portion 108 (FIG. 6) of the heart valve annulus 30. As such, the metallic wire 100" only adds rigidity and strength to the posterior portion 108 of the annuloplasty prosthesis 80". As such, upon implantation, the annuloplasty prosthesis 80" adds rigidity to both the posterior portion 106 and to a lesser degree supports the anterior portion 108 of heart valve annulus 30. In other respects, the annuloplasty prosthesis 80" functions in a similar manner as described above with respect to the annuloplasty prosthesis 80 and 80'.

In general, a cardiac repair device (e.g., a prosthetic heart valve, an annuloplasty prosthesis, a vascular graft, etc.) including a pharmacological delivery implement according to the present invention allows pharmacological agents to be delivered to the heart or vascular member to which the cardiac repair device is attached. Delivery of a pharmacological agent to the heart or vascular member prevents or decreases the occurrence of excess inflammation, excess scar tissue growth, stenosis, and regurgitation. By reducing inflammation, scar tissue growth, stenosis, and regurgitation, use of the pharmacological delivery implement decreases the number of cases in which extraction of the previously implanted cardiac repair device is necessary as well as the emergency cases in which extraction of such a cardiac repair device cannot be performed prior to excessive inflammation, scar tissue growth, stenosis, or regurgitation causing dire consequences.

As such, use of the pharmacological delivery agent within the cardiac repair device as described above, prevents or decreases dangers inherent in stenosis and regurgitation as well as dangers associated with additional patient surgery, such as anesthesia, infection, additional heart stoppage time, blood loss, etc. As such, providing the pharmacological agent to the heart or vascular tissue decreases overall complications associated with cardiac repair as well as contributing to the overall well being of the patient.

Although the present invention has been described with reference to preferred embodiments, workers skilled in the art will recognize that changes can be made in form and detail without departing from the spirit and scope of the present invention.

What is claimed is:

1. A device for implantation comprising:
a heart valve prosthesis;
a porous member formed of a porous material defining pores,
the porous member defining an outer surface having an inflow side and an outflow side opposite the inflow side, the outer surface defining at least one injection site,
the porous member comprising an internal channel having a lumen configured to selectively maintain an injectable pharmacological agent,
wherein the outflow side includes a plurality of release holes in addition to the pores of the member, each of the release holes extending from the outer surface to the internal channel,
wherein the release holes are sized to allow release of the pharmacological agent, and a size of the release holes is greater than a size of the pores,
wherein the pores are located on the inflow and outflow sides,
wherein the release holes do not extend to the inflow side, and
wherein the at least one injection site provides access to the internal channel from the outer surface for injecting the pharmacological agent into the internal channel; and
a fabric sheath encompassing the porous member.

2. The device of claim 1, wherein the porous member has a porosity low enough to maintain the pharmacological agent.

3. The device of claim 1, wherein the porous member has a porosity relative to a viscosity of the pharmacological agent to maintain at least a portion of the pharmacological agent within the internal channel for a desired time period.

4. The device of claim 1, wherein the porous member has a porosity relative to an elution profile of the pharmacological agent to maintain at least a portion of the pharmacological agent within the internal channel for a desired time period.

5. A device comprising:
a heart valve prosthesis;
a porous member formed of a porous material defining pores, the porous member defining:
an outer surface having an inflow side and an outflow side opposite the inflow side;
an internal channel configured to selectively maintain an injectable pharmacological agent; and
at least one injection site providing access to the internal channel from the outer surface for injecting the pharmacological agent into the internal channel,
wherein the outflow side includes a plurality of release holes in addition to the pores in the member, each of the release holes extending from the outer surface to the internal channel,
wherein the release holes are sized to allow release of the pharmacological agent, and a size of the release holes is greater than a size of the pores,
wherein the pores are located on the inflow and outflow sides, and
wherein the release holes do not extend to the inflow side;
a fabric sheath encompassing the porous member; and
a pharmacologic agent selectively maintained within the internal channel.

6. The device of claim 5, wherein the pharmacological agent is maintained within the internal channel in a flowable state.

7. A device for implantation comprising:
a heart valve prosthesis; and
a pharmacological delivery implement comprising a porous member formed of a porous material defining pores, the porous member defining:
an outer surface having an inflow side and an outflow side opposite the inflow side;
an internal channel comprising an unfilled lumen configured to selectively maintain an injectable pharmacological agent; and
at least one injection site defined by the outer surface,
wherein the outflow side of the porous member includes a plurality of release holes in addition to the pores in the member, each of the release holes extending from the outer surface to the internal channel,
wherein the release holes are sized to allow release of the pharmacological agent, and a size of the release holes is greater than a size of the pores,
wherein the pores are located on the inflow and outflow sides,
wherein the release holes do not extend to the inflow side,
wherein the at least one injection site provides access to the internal channel from the outer surface for injecting the pharmacological agent into the internal channel, and
wherein the porous member is formed of silicone or an elastomeric polymer.

8. The device of claim 7, wherein the porous member has a porosity low enough to maintain the pharmacological agent.

9. The device of claim 7, wherein the porous member has a porosity relative to a viscosity of the pharmacological agent to maintain at least a portion of the pharmacological agent within the internal channel for a desired time period.

10. The device of claim 7, wherein the porous member has a porosity relative to an elution profile of the pharmacological agent to maintain at least a portion of the pharmacological agent within the internal channel for a desired time period.

11. A method of delivering a pharmacological agent to cardiac tissue, the method comprising:
providing a device comprising a heart valve prosthesis and a porous member formed of a porous material defining pores, the porous member defining:
  an internal channel with an unfilled lumen, wherein the lumen is configured to selectively maintain a pharmacological agent;
an outer surface; and
  at least one injection site extending from the outer surface to the internal channel,
  wherein the outer surface having an inflow side and an outflow side opposite the inflow side,
  wherein the outflow side includes a plurality of release holes in addition to the pores in the member, each of the release holes extending from the outer surface to the internal channel,
  wherein the release holes are sized to allow release of the pharmacological agent, and a size of the release holes is greater than a size of the pores,
  wherein the pores are located on the inflow and outflow sides,
  wherein the release holes do not extend to the inflow side; and implanting the device within a cardiac system, wherein the lumen is filled by injecting a pharmacological agent via the at least one injection site,
wherein upon functioning of the cardiac system, at least a portion of the pharmacological agent exits the lumen via the plurality of release holes.

12. The method of claim 11, further comprising:
storing the device prior to injecting the pharmacological agent, which in turn occurs prior to implanting the device.

13. The method of claim 11, further comprising:
injecting the pharmacological agent prior to storing the device.

14. The method of claim 11, wherein, upon functioning of the cardiac system, fluid flow from the inflow side to the outflow side of the outer surface facilitates the exit of at least a portion of the pharmacological agent from the lumen.

* * * * *